US008318650B2

(12) United States Patent
Hätzelt et al.

(10) Patent No.: US 8,318,650 B2
(45) Date of Patent: Nov. 27, 2012

(54) BIS(HYDROXYQUINOLINE) METAL COMPLEXES AS BLEACH CATALYSTS

(75) Inventors: Andre Hätzelt, Düsseldorf (DE); Anette Nordskog, Sandefjord (NO); Stefan Leopold, Düsseldorf (DE); Peter Schmiedel, Düsseldorf (DE); Wolfgang von Rybinski, Düsseldorf (DE); Jörg Sundermeyer, Marburg (DE); Jan Döring, Marburg (DE)

(73) Assignee: Henkel AG & Co. KGaA (DE)

( * ) Notice: Subject to any disclaimer, the term of this patent is extended or adjusted under 35 U.S.C. 154(b) by 510 days.

(21) Appl. No.: 12/577,450

(22) Filed: Oct. 12, 2009

(65) Prior Publication Data
US 2010/0048447 A1    Feb. 25, 2010

Related U.S. Application Data

(63) Continuation of application No. PCT/EP2008/054349, filed on Apr. 10, 2008.

(30) Foreign Application Priority Data

Apr. 12, 2007    (DE) .................. 10 2007 017 654

(51) Int. Cl.
C11D 1/00    (2006.01)
C11D 3/20    (2006.01)
C11D 3/28    (2006.01)

(52) U.S. Cl. ........ 510/311; 510/376; 510/465; 510/466; 510/467; 510/499; 510/500; 510/504; 502/200; 502/324; 502/325; 252/186.33

(58) Field of Classification Search .................. 510/311, 510/376, 465, 466, 467, 499, 500, 504; 502/200, 502/324, 325; 252/186.33
See application file for complete search history.

(56) References Cited

U.S. PATENT DOCUMENTS

| | | | |
|---|---|---|---|
| 5,614,161 A | 3/1997 | Wilkens et al. | |
| 5,705,169 A | 1/1998 | Stein et al. | |
| 5,730,960 A | 3/1998 | Stein et al. | |
| 6,294,273 B1 | 9/2001 | Heuer et al. | |
| 6,379,394 B1 | 4/2002 | Chilou et al. | |
| 6,417,151 B1 | 7/2002 | Grothus et al. | |
| 6,541,233 B1 | 4/2003 | Hillen et al. | |
| 7,153,818 B2 | 12/2006 | Breves et al. | |
| 7,262,042 B2 | 8/2007 | Weber et al. | |
| 7,300,782 B2 | 11/2007 | Breves et al. | |
| 7,303,905 B2 | 12/2007 | Breves et al. | |
| 7,320,887 B2 | 1/2008 | Kottwitz et al. | |
| 7,449,187 B2 | 11/2008 | Weber et al. | |
| 7,510,859 B2 | 3/2009 | Wieland et al. | |
| 7,569,226 B2 | 8/2009 | Weber et al. | |
| 2004/0235125 A1 | 11/2004 | Kottwitz et al. | |
| 2004/0259222 A1 | 12/2004 | Breves et al. | |
| 2005/0009167 A1 | 1/2005 | Weber et al. | |
| 2005/0026269 A1 | 2/2005 | Kottwitz et al. | |
| 2005/0049165 A1 | 3/2005 | Kottwitz et al. | |
| 2005/0282261 A1 | 12/2005 | Sauter et al. | |
| 2007/0128129 A1 | 6/2007 | Stehr et al. | |
| 2009/0120555 A1 | 5/2009 | Breves et al. | |
| 2009/0156454 A1 | 6/2009 | Schmiedel et al. | |
| 2009/0170745 A1 | 7/2009 | Merkel et al. | |
| 2009/0227626 A1 | 9/2009 | Deraeve et al. | |

FOREIGN PATENT DOCUMENTS

| | | |
|---|---|---|
| CA | 2306376 A1 | 10/2000 |
| CA | 2326758 A1 | 5/2001 |
| DE | 2054019 A1 | 10/1971 |
| DE | 2650764 A | 5/1977 |
| DE | 19507522 A1 | 9/1996 |
| DE | 19601063 A1 | 9/1996 |
| DE | 19712033 A1 | 9/1998 |
| DE | 19825737 A1 | 12/1999 |
| DE | 19918267 A1 | 10/2000 |
| DE | 10138753 A1 | 3/2003 |
| DE | 102005053529 A1 | 6/2007 |
| DE | 102006018780 A1 | 10/2007 |
| DE | 102006022216 A1 | 11/2007 |
| DE | 102006022224 A1 | 11/2007 |
| EP | 0357280 B1 | 2/1996 |
| EP | 0728749 A2 | 8/1996 |
| EP | 0693471 B1 | 1/1998 |
| EP | 0694521 B1 | 1/1998 |
| EP | 0818450 A1 | 1/1998 |
| EP | 0964459 A2 | 12/1999 |
| GB | 1539779 | 2/1979 |
| JP | 2000048956 A | 2/2000 |
| WO | WO-9102792 A1 | 3/1991 |
| WO | WO-9221760 A1 | 12/1992 |
| WO | WO-9523221 A1 | 8/1995 |
| WO | WO-9532232 A1 | 11/1995 |
| WO | WO-9604940 A1 | 2/1996 |
| WO | WO-9629397 A1 | 9/1996 |
| WO | WO-9634092 A2 | 10/1996 |

(Continued)

OTHER PUBLICATIONS

Yamamoto et al, "Syntheses and Electronic Spectra of 2,2'-Isopropylidenedi-8-quinolinol, Its Nickel(II) and Copper(III) chelates", Bulletin of the Chemical Society of Japan, vol. 51(12), 3489-3495, (1978).*

Yamamoto et al, Syntheses and Electronic Spectra of 4,4'-diacetyl-2,2'-isopropylidenedi 8-quinolinol, Its Nickel(II), Copper(II), and Zinc(II) chelates, Bulletin of the Chemical Society of Japan, vol. 53, 809-810, (1980).*

Fagan, et al., "Using Intelligent/Random Library Screening to Design Focused Libraries for the Optimization of Homogeneous Catalysts: Ullmann Ether Formation". J. Am. Chem. Soc. 2000, vol. 122, pp. 5043-5051.

Stockwell, et al. "Chemical Genetic and Genomic Approaches Reveal a Role for Copper in Specific Gene Activation". J. Am. Chem. Soc. 1999, vol. 121, pp. 10662-10663.

Agustin et al., "Stable heterocyclic (Schiff base) divalent Group 14 element species M-O-Schiff base-O (M = Ge, Sn, Pb)". Journal of Organometallic Chemistry, vol. 592, pp. 1-10. (Jul. 1999).

(Continued)

Primary Examiner — Gregory DelCotto
(74) Attorney, Agent, or Firm — Connolly Bove Lodge & Hutz LLP

(57) ABSTRACT

Bis(hydroxyquinoline)-metal complexes and the use thereof as bleach catalysts are described.

11 Claims, No Drawings

FOREIGN PATENT DOCUMENTS

| | | |
|---|---|---|
| WO | WO-9714804 A1 | 4/1997 |
| WO | WO-9724177 A1 | 7/1997 |
| WO | WO-9703108 A1 | 8/1997 |
| WO | WO-9812307 A1 | 3/1998 |
| WO | WO-9845398 A1 | 10/1998 |
| WO | WO-9906573 A1 | 2/1999 |
| WO | WO-0138471 A1 | 5/2001 |
| WO | WO-0210356 A2 | 2/2002 |
| WO | WO-0244350 A2 | 6/2002 |
| WO | WO-02088340 A2 | 11/2002 |
| WO | WO-03002711 A2 | 1/2003 |
| WO | WO-03038082 A2 | 5/2003 |
| WO | WO-03054177 A2 | 7/2003 |
| WO | WO-03054184 A1 | 7/2003 |
| WO | WO-03054185 A1 | 7/2003 |
| WO | WO-03055974 A2 | 7/2003 |
| WO | WO-03056017 A2 | 7/2003 |
| WO | WO-2004007461 A1 | 1/2004 |
| WO | WO-2004058955 A2 | 7/2004 |
| WO | WO-2004058961 A1 | 7/2004 |
| WO | WO-2005056782 A2 | 6/2005 |
| WO | WO-2005124012 A1 | 12/2005 |
| WO | WO-2007015017 A2 | 2/2007 |
| WO | WO-2008135337 A1 | 11/2008 |

OTHER PUBLICATIONS

Wang et al. "Novel thermal reactions of two geometrical isomers of [Ru(OAc)(2cqn)2NO](H2cqn= 2-chloro-8-quinolinol)". Inorganica Chimica Acta, vol. 321, 2001, 215-220.

K.H.Wallhauser in "Praxis der Sterilisation, Desinfektion—Konservierung: Keimidentifizierung—Betriebshygiene". 5-th Ed. Stuttgart; New York: Thieme, 1995, pp. 465-520.

K.N. Wallhauser in "Praxis der Sterilisation, Desinfektion—Konservierung: Keimidentifizierung—Betriebshygiene". 5-th Ed., Stuttgart; New York: Thieme, 1995, pp. 529-588.

K.H.Wallhauser in "Praxis der Sterilisation, Desinfektion—Konservierung: Keimidentifizierung—Betriebshygiene". 5-th Ed., Stuttgart; New York: thieme, 1995, pp. 596-562.

Finkel, "Formulierung kosmetischer Sonnenschutzmittel". SOFW-Journal, vol. 122, 1996, pp. 543-548.

\* cited by examiner

BIS(HYDROXYQUINOLINE) METAL COMPLEXES AS BLEACH CATALYSTS

CROSS-REFERENCE TO RELATED APPLICATIONS

This application is a continuation of and claims benefit of priority under 35 U.S.C. §120 of International Application No. PCT/EP2008/054349, filed on Apr. 10, 2008 (designating the U.S.), which in turn claims priority under 35 U.S.C. §119(a)-(d) of German Application No. DE 102007017654.8, filed on Apr. 12, 2007, the entire contents of each of which are incorporated herein by reference.

BACKGROUND OF THE INVENTION

For effective bleaching with hydrogen peroxide, the latter must be converted into a species having more bleaching activity. One possibility for generating activated peroxy compounds is the use of peracid precursors, so-called "bleach activators" such as TAED, that are converted by perhydrolysis into the active species.

A further possibility for generating activated species is enzymatically catalyzed perhydrolysis of carboxylic acid esters or nitrile compounds using perhydrolases.

Lastly, it is also known to use bleach catalysts to generate activated species, a "bleach catalyst" being understood as a substance that can improve the bleaching performance of hydrogen peroxide on a bleachable material without itself participating stoichiometrically in the reaction.

The use of bleach catalysts has the advantage, as compared with the other bleach activation methods, that substoichiometric quantities of the compound are sufficient, with the result that space and weight can be saved in the formulation of the bleach-containing product. In addition, the reduction in weight, especially in the context of washing and cleaning applications, is also associated with the advantage that less material is discharged into the environment, which is particularly advantageous for ecological reasons. Transportation and packaging costs can also be reduced as a result.

Consideration must also be given to the fact that premature hydrolysis can occur when bleach activators such as nitriles or TAED are used in the presence of water, whereas this problem can be very largely eliminated with the use of bleach catalysts. Furthermore, the production of acids that occurs in the context of noncatalytic bleach activation based on peracids causes a shift in pH that can have an unfavorable effect on bleaching performance. In addition, the bleaching performance of most bleach activators at low temperatures is often unsatisfactory.

For the reasons cited above, the use of bleach catalysts is of particular interest as compared with the other techniques for bleach activation, so that a demand exists in principle for novel bleach catalysts.

Bleach catalysts that have been described are, in particular, metal complexes of organic ligands such as salenes, saldimines, tris[salicylideneaminoethyl]amines, monocyclic polyazaalkanes, cross-bridged polycyclic polyazaalkanes, terpyridines, and tetraamido ligands. A disadvantage of the metal complexes just described is, however, that they either they do not possess sufficient bleaching performance especially at low temperature, or that, with sufficient bleaching performance, undesirable damage occurs to colors and, in some cases, also to textile fibers.

N-Alkyl-2,2'-imino-bis-(8-hydroxyquinoline)-metal complexes are already described in the existing art. DE19825737, for example, describes zinc, magnesium, aluminum, gallium, indium, and lutetium complexes of such ligands, and the use of said complexes in an electroluminescent arrangement. Agustin et al. (J. Org. Chem. 592 (1999) 1-10) describe germanium and tin complexes of N-methyl-2,2'-imino-bis(8-hydroxyquinoline), and Fagan et al. (J. Am. Chem. Soc. 122 (2000) 5043-5051) describe the copper complex of this ligand and an investigation of its property of phenoxylating 2-bromo-4,6-dimethylanilines. Stockwell et al. (J. Am. Chem. Soc. 121 (1999) 10662-10663) investigate the influence of N-methyl-2,2'-imino-bis(8-hydroxyquinoline) on the expression of different genes in Saccharomyces cerevisiae, and additionally investigate the complex-forming constants of this ligand with reference to various metal ions.

Wang et al. (inorganica Chimica Acta 321 (2001) 215-220) describe ruthenium complexes of bis(8-hydroxyquinolin-2-yl)ether. DE2650764 describes the use of 2,2'-methylene-bis (8-hydroxyquinoline) as a polyfunctional coupler for the development of color images.

Use of the ligands and metal-ligand complexes as bleach catalysts, or as an additive for washing and cleaning agents, is not described in the aforesaid documents.

BRIEF SUMMARY OF THE INVENTION

The present invention relates to bis(hydroxyquinoline)-metal complexes and to the use thereof as bleach catalysts.

It has now been found, surprisingly, that bis(hydroxyquinoline)-metal complexes are outstandingly suitable as an oxidation catalyst, and at the same time behave more gently with respect to laundry than the presently usual bleach catalysts.

A first subject of the present invention is therefore washing and cleaning agents containing ligands, and/or metal-ligand complexes of ligands, of the general formula (I)

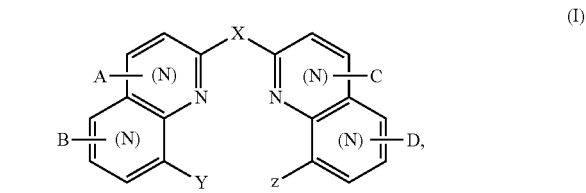

wherein (N) means that one or two CH groups of the corresponding aryl residue can optionally be replaced by H.

The basic structure can be selected in this context, in particular, from:

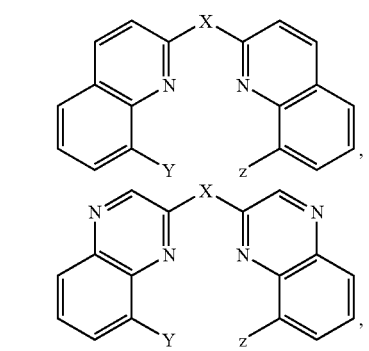

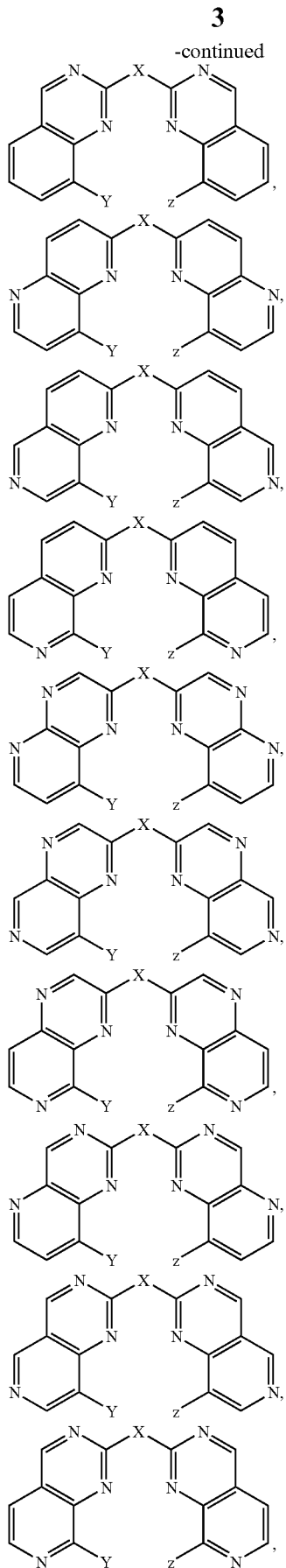

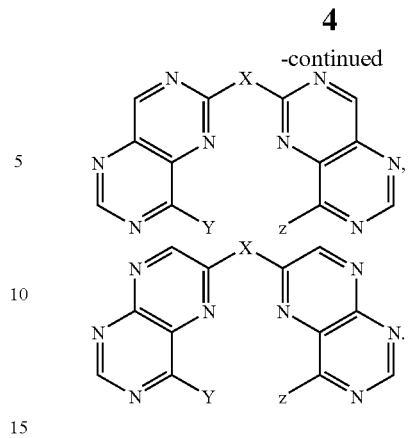

Ligands of the general formula (II)

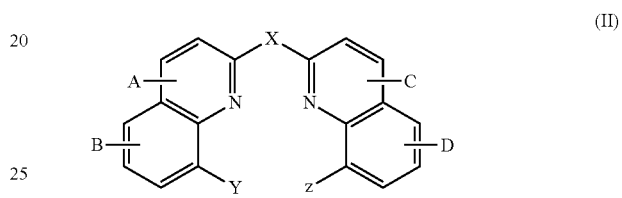

are preferred.

Bishydroxyquinolines of the general formula (III)

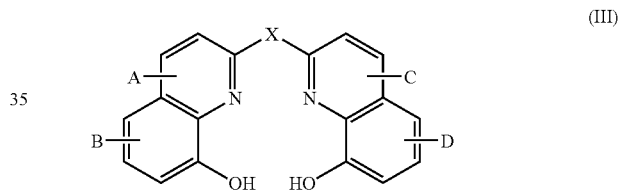

are particularly preferred.

In the formulas:

X denotes $NR^1$, $NR^1R^{2(+)}$, $PR^1$, $PR^1R^{2(+)}$, $P(O)R^1$, O, S, $BR^1$, $BR^1R^{2(-)}$, $CR^3R^4$, or $SiR^3R^4$, Y and Z, mutually independently, denote OH, SH, $NH_2$, $NHR^5$, or $NR^5R^6$, A, B, C, D, $R^1$, $R^2$, $R^3$, and $R^4$, mutually independently, denote hydrogen, alkyl, in particular $C_{1-22}$ alkyl, by preference $C_{11-18}$ alkyl, trifluoromethyl, cycloalkyl, in particular $C_{3-8}$ cycloalkyl, cycloalkylalkyl, in particular $C_{3-8}$ cycloalkyl-$C_{1-12}$ alkyl, alkenyl, in particular $C_{2-18}$ alkenyl, alkinyl, in particular $C_{2-18}$ alkinyl, heteroalkyl, heterocycloalkyl, alkoxy, in particular $C_{1-18}$ alkoxy, alkylsulfanyl, in particular $C_{1-18}$ alkylsulfanyl, alkylsulfinyl, in particular $C_{1-18}$ alkylsulfinyl, alkylsulfonyl, in particular $C_{1-18}$ alkylsulfonyl, alkanoyl, in particular $C_{1-18}$ alkanoyl, alkanoyloxy, in particular $C_{1-18}$ alkanoyloxy, alkoxycarbonyl, in particular $C_{1-18}$ alkoxycarbonyl, alkylaminocarbonyl, in particular $C_{1-18}$ alkylaminocarbonyl, alkylsulfanylcarbonyl, in particular $C_{1-18}$ alkylsulfanylcarbonyl, hydroxy, amino, aryl, in particular $CO_{6-10}$ aryl, arylalkyl, in particular $C_{6-10}$ aryl-$C_{1-12}$ alkyl, aryloxy, in particular $C_{6-10}$ aryloxy, arylsulfanyl, in particular $C_{6-10}$ arylsulfanyl, arylsulfinyl, in particular $C_{6-10}$ arylsulfinyl, arylsulfonyl, in particular $C_{6-10}$ arylsulfonyl, arylcarbonyl, in particular $C_{6-10}$ arylcarbonyl, arylcarbonyloxy, in particular $C_{6-10}$ arylcarbonyloxy, aryloxycarbonyl, in particular $C_{6-10}$ aryloxycarbonyl, arylaminocarbonyl, in particular $C_{6-10}$ arylaminocarbonyl, arylsulfanylcarbonyl, in particular $C_{6-10}$ arylsulfanylcarbonyl, heteroaryl, heteroarylalkyl, in particular heteroaryl-$C_{1-12}$ alkyl, heteroaryloxy, heteroarylamino, heteroarylsulfanyl, heteroarylsulfonyl, heteroarylsulfoxidyl, heteroarylcarbonyl, heteroarylcarbonyloxy, heteroaryloxycarbonyl, heteroarylaminocarbonyl, heteroarylsulfanylcarbonyl, alkoxysulfonyl, in particular $C_{1-18}$ alkoxysulfonyl, alkoxycarbinol, in particular $C_{1-12}$ alkoxycarbinol, ammonium, hydroxycarbonyl, alkoxycarbonyl, in particular $C_{1-18}$ alkoxycarbonyl, aryloxycarbonyl, in particular $C_{6-10}$ aryloxycarbonyl, amidocarbonyl, halogen, in particular chlorine, bromine, iodine or fluorine, nitro, sulfato, sulfo, amidosulfo, phosphato, phosphono, amidophosphono, formyl, thioformyl, —(CH$_2$—CH$_2$—O—)$_n$H and —(CH$_2$—CH$_2$—CH$_2$—O)$_n$H where n=1 to 20, by preference 3 to 20, $R^5$ and $R^6$, mutually independently, denote hydrogen or alkyl, in particular $C_{1-18}$ alkyl, wherein all residues of the so resulting molecule, in particular the aliphatic and aromatic residues, mutually independently in each case, can optionally also be mono- or poly-, in particular mono-, di-, or trisubstituted, by preference monosubstituted, in particular with substituents selected from the residues cited above.

In a preferred embodiment, A, B, C, D, $R^3$, $R^4$, $R^5$, and $R^6$ have the meanings recited above and $R^1$ and $R^2$, mutually independently, denote hydrogen, alkyl, in particular $C_{1-22}$ alkyl, by preference $C_{1-18}$ alkyl, cycloalkyl, in particular $C_{3-8}$-cycloalkyl, cycloalkylalkyl, in particular $C_{3-8}$-cycloalkyl-$C_{1-12}$ alkyl, alkenyl, in particular $C_{2-18}$ alkenyl, alkinyl, in particular $C_{2-18}$ alkinyl, heteroalkyl, heterocycloalkyl, alkanoyl, in particular $C_{1-18}$ alkanoyl, alkoxycarbonyl, in particular $C_{1-18}$ alkoxycarbonyl, alkylaminocarbonyl, in particular $C_{1-18}$ alkylaminocarbonyl, alkylsulfanylcarbonyl, in particular $C_{1-18}$ alkylsulfanylcarbonyl, aryl, in particular $C_{6-10}$ aryl, arylalkyl, in particular $C_{6-10}$ aryl-$C_{1-12}$ alkyl, arylcarbonyl, in particular $C_{6-10}$ arylcarbonyl, aryloxycarbonyl, in particular $C_{6-10}$ aryloxycarbonyl, arylaminocarbonyl, in particular $C_{6-10}$ arylaminocarbonyl, arylsulfanylcarbonyl, in particular $C_{6-10}$ arylsulfanylcarbonyl, heteroaryl, heteroarylalkyl, in particular heteroaryl-CO$_{1-12}$ alkyl, heteroarylcarbonyl, heteroaryloxycarbonyl, heteroarylaminocarbonyl, heteroarylsulfanylcarbonyl, trifluoromethyl, formyl, —(CH$_2$—CH$_2$—O—)$_n$H or —(CH$_2$—CH$_2$—CH$_2$—O)$_n$H where n=1 to 20, wherein all residues of the so resulting molecule, in particular the aliphatic and aromatic residues, mutually independently in each case, can optionally also be mono- or poly-, in particular mono-, di-, or trisubstituted, by preference monosubstituted, in particular with substituents selected from the residues cited above, and selected from ammonium, hydroxycarbonyl, alkoxycarbonyl, in particular $C_{1-18}$ alkoxycarbonyl, aryloxycarbonyl, in particular $C_{6-10}$ aryloxycarbonyl, amidocarbonyl, halogen, in particular chlorine, bromine, iodine, or fluorine, nitro, sulfato, sulfo, amidosulfo, phosphate, phosphono, amidophosphono, hydroxy, alkoxy, in particular $C_{1-18}$ alkoxy, amino, and alkanoyloxy, in particular $C_{1-18}$ alkanoyloxy.

In a further preferred embodiment, X denotes NR$^1$, NR$^1$R$^{2(+)}$, PR$^1$, or PR$^1$R$^{2(+)}$, and A, B, C, D, Y, Z, $R^1$, $R^2$, $R^3$, $R^4$, $R^5$, and $R^6$ have the meanings recited above.

In a further preferred embodiment, Y and Z denote OH, and A, B, C, D, X, $R^1$, $R^2$, $R^3$, $R^4$, $R^5$, and $R^6$ have the meanings recited above.

In a particularly preferred embodiment,
X denotes NR$^1$, NR$^1$R$^{2(+)}$, PR$^1$, PR$^1$R$^{2(+)}$ or S,
Y and Z denote OH,
$R^1$ and $R^2$, mutually independently, denote hydrogen, $C_{1-6}$ alkyl, —(CH$_2$—CH$_2$—O—)$_n$H or —(CH$_2$—CH$_2$—CH$_2$—O)$_n$H where n=1 bis 20, A, B, C, and D, mutually independently, denote hydrogen, alkyl, in particular $C_{1-18}$ alkyl, ammonium, hydroxycarbonyl, alkoxycarbonyl, in particular $C_{1-18}$ alkoxycarbonyl, aryloxycarbonyl, in particular $C_{6-10}$ aryloxycarbonyl, amidocarbonyl, halogen, in particular chlorine, bromine, iodine, or fluorine, nitro, sulfato, sulfo, amidosulfo, phosphate, phosphono, amidophosphono, hydroxy, alkoxy, in particular $C_{1-18}$ alkoxy, or amino, wherein all residues of the so resulting molecule, mutually independently in each case, can optionally also be mono- or poly-, in particular mono-, di-, or trisubstituted, by preference monosubstituted, in particular with substituents selected from the residues cited above.

In a further preferred embodiment, at least one of the residues A, B, C, D, and X encompasses at least one group selected from ammonium, nitro, sulfato, sulfo, amidosulfo, hydroxycarbonyl, alkoxycarbonyl, aryloxycarbonyl, amidocarbonyl, phosphate, phosphono, amidophosphono, hydroxy, alkoxy, amino, polyoxyethylene, and halogen as substituents, wherein the residue can be selected in this context, in particular, from sulfo, sulfoalkyl, in particular sulfo-$C_{1-18}$ alkyl, hydroxycarbonyl, hydroxycarbonylalkyl, in particular hydroxycarbonyl-$C_{1-18}$ alkyl, phosphono, phosphonoalkyl, in particular phosphono-$C_{1-18}$ alkyl, hydroxy, hydroxyalkyl, in particular hydroxy-$C_{1-18}$ alkyl, amino, aminoalkyl, in particular amino-$C_{1-18}$ alkyl, halogen, haloalkyl, in particular halo-$C_{1-18}$ alkyl, —(CH$_2$—CH$_2$—O—)$_n$H, and $C_{1-18}$ alkyl-(CH$_2$—CH$_2$—O—)$_n$H, where in each case n=1 to 20, by preference 3 to 20.

DETAILED DESCRIPTION OF THE INVENTION

"$C_{1-18}$ alkyl" denotes according to the present invention, mutually independently in each case, all saturated linear and branched alkyl residues having up to 18 carbon atoms, $C_{1-16}$ alkyl residues being preferred. "$C_{1-6}$ alkyl" denotes according to the present invention all saturated linear and branched alkyl residues having up to 6 carbon atoms, in particular methyl, ethyl, n-propyl, isopropyl, n-butyl, isobutyl, tert-butyl, and all isomers of pentyl and hexyl.

"$C_{3-8}$ cycloalkyl" denotes according to the present invention, mutually independently in each case, all cyclic alkyl residues having 3 to 8 carbon atoms, by preference having 5 to 6 carbon atoms, wherein the residues can be saturated or unsaturated, in particular cyclopentyl, cyclohexyl, or cyclopentadienyl.

"$C_{2-18}$ alkenyl" denotes according to the present invention, mutually independently in each case, all linear and branched alkyl residues, having up to 18 carbon atoms, that contain at least one double bond, $C_{2-6}$ alkenyl residues being preferred. "$C_{2-6}$ alkenyl" denotes according to the present invention all linear and branched alkyl residues, having up to 6 carbon atoms, that contain at least one double bond, in particular ethenyl, propenyl, isopropenyl, and all isomers of butenyl, pentenyl, and hexenyl.

"$C_{2-18}$ alkinyl" denotes according to the present invention, mutually independently in each case, all linear and branched alkyl residues, having up to 18 carbon atoms, that contain at least one triple bond, $C_{2-6}$ alkinyl residues being preferred. "$C_{2-8}$ alkinyl" denotes according to the present invention all linear and branched alkyl residues, having up to 6 carbon atoms, that contain at least one triple bond, in particular ethinyl, propinyl, isopropinyl, and all isomers of butinyl, pentinyl, and hexinyl.

"Heteroalkyl" denotes according to the present invention, mutually independently in each case, all saturated and mono- or polyunsaturated, linear or branched alkyl residues that contain at least one, preferably exactly one, heteroatom, selected in particular from O, S, and N, the sum of carbon atoms and heteroatoms preferably equaling up to 18, particularly preferably up to 6.

"Heterocycloalkyl" denotes according to the present invention, mutually independently in each case, all cyclic alkyl radicals that contain at least one, preferably exactly one, heteroatom, selected in particular from O, S, and N, the ring having by preference three to eight members, particularly preferably five to six members. Examples thereof are tetrahydrofuranyl, tetrahydrothiophenyl, pyrrolidinyl, 2-thiazolinyl, tetrahydrothiazolyl, tetrahydrooxazolyl, piperidinyl, piperazinyl, morpholinyl, and thiomorpholinyl.

"$C_{1-18}$ alkoxy" denotes according to the present invention, mutually independently in each case, all saturated and unsaturated, linear and branched alkyl residues, having up to 18 carbon atoms, that are bound via an oxygen atom, $C_{1-6}$ alkoxy residues being preferred. "$C_{1-6}$ alkoxy" denotes according to the present invention, mutually independently in each case, all saturated and unsaturated, linear and branched alkyl residues, having up to 6 carbon atoms, that are bound via an oxygen atom, in particular methoxy and ethoxy.

"$C_{1-18}$ alkylsulfanyl" denotes according to the present invention, mutually independently in each case, all saturated and unsaturated, linear and branched alkyl residues, having up to 18 carbon atoms, that are bound via a sulfur atom, $C_{1-6}$ alkylsulfanyl residues being preferred. "$C_{1-6}$ alkylsulfanyl" denotes according to the present invention all saturated and unsaturated, linear and branched alkyl residues, having up to 6 carbon atoms, that are bound via a sulfur atom, in particular methylsulfanyl and ethylsulfanyl.

"$C_{1-18}$ alkylsulfinyl" denotes according to the present invention, mutually independently in each case, all saturated and unsaturated, linear and branched alkyl residues, having up to 18 carbon atoms, that are bound via an SO— group, $C_{1-6}$ alkylsulfinyl residues being preferred. "$C_{1-6}$ alkylsulfinyl" denotes according to the present invention all saturated and unsaturated, linear and branched alkyl residues, having up to 6 carbon atoms, that are bound via an SO— group, in particular methylsulfinyl and ethylsulfinyl.

"$C_{1-18}$ alkylsulfonyl" denotes according to the present invention, mutually independently in each case, all saturated and unsaturated, linear and branched alkyl residues having up to 18 carbon atoms that are bound via an $SO_2$— group, $C_{1-6}$ alkylsulfonyl residues being preferred. "$C_{1-6}$ alkylsulfonyl" denotes according to the present invention all saturated and unsaturated, linear and branched alkyl residues, having up to 6 carbon atoms, that are bound via an $SO_2$— group, in particular methylsulfonyl and ethylsulfonyl.

"$C_{1-18}$ alkanoyl" denotes according to the present invention, mutually independently in each case, all saturated and unsaturated, linear and branched alkyl residues, having up to 18 carbon atoms, that are bound via a carbonyl group, $C_{1-6}$ alkanoyl residues being preferred. "$C_{1-6}$ alkanoyl" denotes according to the present invention all saturated and unsaturated, linear and branched alkyl residues, having up to 6 carbon atoms, that are bound via a carbonyl group, in particular methylcarbonyl and ethylcarbonyl.

"$C_{1-18}$ alkanoyloxy" denotes according to the present invention, mutually independently in each case, all saturated and unsaturated, linear and branched alkyl residues, having up to 18 carbon atoms, that are bound via a carbonyloxy group, $C_{1-6}$ alkanoyloxy residues being preferred. "$C_{1-6}$ alkanoyloxy" denotes according to the present invention all saturated and unsaturated, linear and branched alkyl residues, having up to 6 carbon atoms, that are bound via a carbonyloxy group, in particular methanoyloxy, ethanoyloxy, n-propanoyloxy, and i-propanoyloxy.

"$C_{1-18}$ alkoxycarbonyl" denotes according to the present invention, mutually independently in each case, all saturated and unsaturated, linear and branched alkyl residues, having up to 18 carbon atoms, that are bound via an oxycarbonyl group, $C_{1-6}$ alkoxycarbonyl residues being preferred. "$C_{1-6}$ alkoxycarbonyl" denotes according to the present invention all saturated and unsaturated, linear and branched alkyl residues, having up to 6 carbon atoms, that are bound via an oxycarbonyl group, in particular methoxycarbonyl and ethoxycarbonyl.

"$C_{1-18}$ alkylaminocarbonyl" denotes according to the present invention, mutually independently in each case, an aminocarbonyl group that is mono- or polysubstituted with a saturated or unsaturated, linear or branched alkyl residue having up to 18 carbon atoms, wherein aminocarbonyl residues mono- or disubstituted with $C_{1-6}$ alkyl groups, in particular monomethylaminocarbonyl, diemethylaminocarbonyl, monoethylaminocarbonyl, and diethylaminocarbonyl, are preferred.

"$C_{1-18}$ alkylsulfanylcarbonyl" denotes according to the present invention, mutually independently in each case, all saturated and unsaturated, linear and branched alkyl residues, having up to 18 carbon atoms, that are bound via a thiocarbonyl group, $C_{1-6}$ alkylsulfanylcarbonyl radicals being preferred. "$C_{1-6}$ alkylsulfanylcarbonyl" denotes according to the present invention all saturated and unsaturated, linear and branched alkyl residues, having up to 6 carbon atoms, that are bound via a thiocarbonyl group, in particular methylthiocarbonyl and ethylthiocarbonyl.

"($C_{1-18}$ alkyl)NH" denotes according to the present invention, mutually independently in each case, all saturated and unsaturated, linear and branched alkyl residues, having up to 18 carbon atoms, that are bound via a hydrogen-amino group, ($C_{1-6}$ alkyl)NH being preferred. "($C_{1-6}$ Alkyl)NH" denotes according to the present invention all saturated and unsaturated, linear and branched alkyl residues, having up to 6 carbon atoms, that are bound via a hydrogen-amino group, in particular $CH_3NH$ and $C_2H_5NH$.

"Di-($C_{1-18}$ alkyl)N" denotes according to the present invention, mutually independently in each case, all saturated and unsaturated, linear and branched alkyl residues, having up to 18 carbon atoms, that are bound via a ($C_{1-18}$ alkyl)amino group, di-($C_{1-6}$ alkyl)N being preferred. The two alkyl residues can, in this context be identical to or different from one another. "Di-($C_{1-6}$ alkyl)N" denotes according to the present invention all saturated and unsaturated, linear and branched alkyl residues, having up to 6 carbon atoms, that are bound via a ($C_{1-6}$ alkyl)amino group, in particular $(CH_3)_2N$ and $(C_2H_5)_2N$.

"$C_{6-10}$ aryl" denotes according to the present invention preferably phenyl or naphthyl, particularly preferably naphthyl, in particular including in $C_{6-10}$ aryl-$C_{1-12}$ alkyl, $C_{6-10}$ aryloxy, $C_{6-10}$ arylamino, $C_{6-10}$ arylsulfanyl, $C_{6-10}$ arylsulfonyl, $C_{6-10}$ arylsulfoxidyl, $C_{6-10}$ arylcarbonyl, $C_{6-10}$ arylcarbonyloxy, $C_{6-10}$ aryloxycarbonyl, $C_{6-10}$ arylaminocarbonyl, and $C_{6-10}$ arylsulfanylcarbonyl.

"Heteroaryl" denotes according to the present invention, unless otherwise indicated, an aromatic residue containing at least one heteroatom selected from O, S, and N, having 5 to 10, by preference 5 or 6 ring members, by preference selected from furanyl, thienyl, thiophenyl, pyrrolyl, isopyrroyl, pyrazolyl, imidazolyl, oxazolyl, thiazolyl, isothiazolyl, pyridinyl, pyridazinyl, pyrimidinyl, pyrazinyl, triazinyl, benzofuranyl, benzothiophenyl, indolyl, quinolinyl, isoquinolinyl, benzimidazolyl, indazolyl, pyridofuranyl, and pyridothienyl, in particular including in heteroaryl-$C_{1-12}$ alkyl, heteroaryloxy, heteroarylamino, heteroarylsulfanyl, heteroarylsulfonyl, heteroarylsulfoxidyl, heteroarylcarbonyl, heteroarylcarbonyloxy, heteroaryloxycarbonyl, heteroarylaminocarbonyl and heteroarylsulfanylcarbonyl.

In $C_{6-10}$ aryl-$C_{1-12}$ alkyl and heteroarylalkyl, the alkyl residue can be saturated or unsaturated, branched or unbranched. Preferred residues are benzyl, phenylethyl, naphthylmethyl, and naphthylethyl.

"Amino" denotes according to the present invention any substituted or unsubstituted amino group, in particular —$NH_2$, —$NH(C_{1-18}$ alkyl), —$N(C_{1-18}$ alkyl)$_2$, —$NH(C_{6-10}$ aryl), or —$N(C_{6-10}$ aryl)$_2$.

"Ammonium" denotes according to the present invention any substituted or unsubstituted ammonium group, in particular —$NH_3^{(+)}$, —$NH_2(C_{1-18}$ alkyl)$^{(+)}$), —$NH(C_{1-18}$ alkyl)$_2^{(+)}$, or —$N(C_{1-18}$ alkyl)$_3^{(+)}$.

"Sulfato" denotes according to the present invention, in particular, —O—S(O)$_2$—O—R, "sulfo" denotes —S(O)$_2$—O—R, "amidosulfo" denotes —O—S(O)$_2$—NR$_2$, "phosphato" denotes —O—P(O)(OR)$_2$, "phosphono" denotes —P(O)(OR)$_2$, "amidophosphono" denotes —O—P(O)(NR$_2$)$_2$ or —O—P(O)(OR)(NR$_2$), and "amidocarbonyl" denotes —C(O)—NR$_2$, wherein R, mutually independently in each case, denotes H, $M^{(+)}$, $C_{1-18}$ alkyl, $C_{6-10}$ aryl, or $C_{1-18}$ alkyl-$C_{6-10}$ aryl.

The metal-ligand complex according to the present invention is by preference a complex with a metal selected from Ag, Al, Ce, Co, Cu, Fe, Mo, Mn, Ni, Pb, Re, Ti, V, and Zn in any oxidation states, the metal being selected by preference from Co(II), Co(III), Cu(I), Cu(II), Fe(II), Fe(III), Mn(II), Mn(III), Ni(II), Pb(II), and Zn(II), particularly preferably from Mn(II) and Mn(III).

The metal-ligand complex can, as a rule be manufactured easily by mixing a metal salt of the corresponding metal with the corresponding ligand in an aqueous environment. The production of a desired oxidation state can be favored by establishing a suitable redox potential.

Any counterion, in particular acetate, tetrafluoroborate, fluoride, bromide, iodide, or chloride, is suitable in principle for saturating the valences still unoccupied, and/or any charge that is still free, after binding to the ligand.

A further subject of the present invention is also the use of washing and cleaning agents according to the present invention for cleaning textile fabrics and for cleaning hard surfaces.

Likewise a subject of the present invention are the aforementioned ligands and metal-ligand complexes according to the present invention as such. The metal-ligand complexes according to the present invention are also hereinafter called "bleach catalysts according to the present invention."

A particular subject of the present invention is in this context, in particular, metal-ligand complexes of ligands of the general formula (I), in particular of the general formula (II), by preference of the general formula (III), wherein the transition metal atom is selected from Ag, Ce, Co, Cu, Fe, Mo, Mn, Ni, Pb, Re, Ti, and V in any oxidation states, in particular from Co(II), Co(III), Cu(I), Cu(II), Fe(II), Fe(III), Mn(II), Mn(III), Ni(II), and Pb(II), particularly preferably from Mn(II) and Mn(III), X denotes $NR^1$, $NR^1R^{2(+)}$, $PR^1$, $PR^1R^{2(+)}$, $P(O)R^1$, O, S, $BR^1$, $BR^1R^2$, $CR^3R^4$, or $SiR^3R^4$, Y and Z, mutually independently, denote OH, SH, $NH_2$, $NHR^5$, or $NR^5R^6$, A, B, C, D, $R^1$, $R^2$, $R^3$, $R^4$, $R^5$, and $R^6$, mutually independently, denote one of the residues recited above, wherein furthermore at least one of the residues A, B, C, D, $R^1$, $R^2$, $R^3$, $R^4$, $R^5$, and $R^6$ denotes a substituent other than hydrogen, at least one of the residues A, B, C, D, $R^1$, $R^2$, $R^3$, $R^4$, $R^5$, and $R^6$ by preference denoting a substituent encompassing a group selected from ammonium, nitro, sulfato, sulfo, amidosulfo, hydroxycarbonyl, alkoxycarbonyl, aryloxycarbonyl, amidocarbonyl, phosphate, phosphono, amidophosphono, hydroxy, alkoxy, amino, polyoxyethylene, and halogen.

A further particular subject of the present invention is metal-ligand complexes of ligands of the general formula (I), in particular of the general formula (II), by preference of the general formula (III), wherein the transition metal atom is selected from Ag, Al, Ce, Co, Cu, Fe, Mo, Mn, Ni, Pb, Re, Ti, U, V, and Zn in any oxidation states, in particular from Co(II), Co(III), Cu(I), Cu(II), Fe(II), Fe(III), Mn(II), Mn(III), Ni(II), Pb(II), U(IV), and Zn(II), particularly preferably from Mn(II) and Mn(III), X denotes $PR^1$, $PR^1R^{2(+)}$, $P(O)R^1$, O, S, $BR^1$, $BR^1R^{2(-)}$, $CR^3R^4$, or $SiR^3R^4$, Y and Z, mutually independently, denote OH, SH, $NH_2$, $NHR^5$, and $NR^5R^6$, A, B, C, D, $R^1$, $R^2$, $R^3$, $R^4$, $R^5$, and $R^6$, mutually independently, denote one of the residues recited above, at least one of the residues A, B, C, D, $R^1$, $R^2$, $R^3$, $R^4$, $R^5$, and $R^6$ by preference denoting a substituent encompassing a group selected from ammonium, nitro, sulfato, sulfo, amidosulfo, hydroxycarbonyl, alkoxycarbonyl, aryloxycarbonyl, amidocarbonyl, phosphate, phosphono, amidophosphono, hydroxy, alkoxy, amino, polyoxyethylene, and halogen.

A further subject of the present invention is also the use of ligands and/or metal-ligand complexes according to the present invention in washing or cleaning agents, in particular for cleaning textile fabrics and for cleaning hard surfaces.

A further subject of the present invention is also the use of ligands and/or metal-ligand complexes according to the present invention, in particular as adjuvants, for cleaning textile fabrics and for cleaning hard surfaces.

A further subject of the present invention is also the use of ligands and/or metal-ligand complexes according to the present invention for bleaching woodpulp and/or raw cotton.

The washing and cleaning agents according to the present invention can be all conceivable types of cleaning agent, both concentrates and agents to be used undiluted, for use on a commercial scale, in a washing machine or for hand laundering or cleaning. These include, for example, washing agents for textiles, carpets, or natural fibers, for which the term "washing agent" is used according to the present invention. These also include, for example, dishwashing agents for automatic dishwashers or manual dishwashing agents, or cleaners for hard surfaces such as metal, glass, porcelain, ceramic, tiles, stone, painted surfaces, plastics, wood, or leather; the term "cleaning agent" is used for these according to the present invention. In the broader sense, sterilization and disinfection agents are also to be regarded as washing and cleaning agents for purposes of the invention.

Embodiments of the present invention encompass all presentation forms established according to the existing art and/or all useful such forms of the washing or cleaning agents according to the present invention. These include, for example, solid, powdered, liquid, gelled, or pasty agents, optionally also made up of multiple phases, compressed or uncompressed; also included thereamong are extrudates, granules, tablets, or pouches, packaged both in large containers and in portions.

In a preferred embodiment, the washing or cleaning agents according to the present invention contain the above-described bleach catalysts according to the present invention in a quantity of up to 5 wt %, in particular from 0.001 wt % to 1 wt %, and particularly preferably from 0.01 wt % to 0.5 wt %, especially from 0.01 to 0.25 wt %, based in each case on the total weight of the washing or cleaning agent.

In addition to the bleach catalysts according to the present invention, other bleach catalysts can also be additionally contained, if applicable, in the agents according to the present invention. These substances can be, in general, any bleach-intensifying transition metal salt or any transition metal complex. Suitable transition metals in this context are, in particular, Mn, Fe, Co, Ru, Mo, Ti, V, or Cu, in different oxidation states. Suitable as possible complexing ligands are in particular, as described in the literature, guanidines, aminophenols, amine oxides, salenes, saldimines, lactams, monocyclic and cross-bridged polycyclic polyazaalkanes, terpyridines, dendrimers, tetraamido ligands, bis- and tetrakis(pyridylmethyl)alkylamines, secondary amines, and polyoxometallates.

In a preferred embodiment, a complex of manganese in oxidation state II, III, IV, or V, that by preference contains one or more macrocyclic ligands having the donor functions N, NR, PR, O, and/or S, is used as an additional bleach catalyst. Ligands that comprise nitrogen donor functions are used by preference in this context. It is particularly preferred in this context to use additionally in the agents according to the present invention a bleach catalyst that contains, as macromolecular ligands, 1,4,7-trimethyl-1,4,7-triazacyclononane (Me-TACN), 1,4,7-triazacyclononane (TACN), 1,5,9-trimethyl-1,5,9-triazacyclododecane (Me-TACD), 2-methyl-1,4,7-trimethyl-1,4,7-triazacyclononane (Me/Me-TACN) and/or 2-methyl-1,4,7-triazacyclononane (Me/TACN). Suitable manganese complexes are, for example, $[Mn^{III}_2(\mu\text{-O})_1(\mu\text{-OAc})_2(TACN)_2](ClO_4)_2$, $[Mn^{III}Mn^{IV}(\mu\text{-O})_2(\mu\text{-OAc})_1(TACN)_2](BPh_4)_2$, $[Mn^{IV}_4(\mu\text{-O})_6(TACN)_4](ClO_4)_4$, $[Mn^{III}_2(\mu\text{-O})_1(\mu\text{-OAc})_2(Me\text{-TACN})_2](ClO_4)_2$, $[Mn^{III}Mn^{IV}(\mu\text{-O})_1(\mu\text{-OAc})_2(Me\text{-TACN})_2](ClO_4)_3$, $[Mn^{IV}_2(\mu\text{-O})_3(Me\text{-TACN})_2](PF_6)_2$, and $[Mn^{IV}_2(\mu\text{-O})_3(Me/Me\text{-TACN})_2](PF_6)_2$ (OAc=OC(O)CH$_3$).

The additional bleach catalyst, if used, is also contained in the agents according to the present invention in a quantity of up to 5 wt %, in particular from 0.0025 wt % to 1 wt %, and particularly preferably from 0.01 wt % to 0.25 wt %, based in each case on the total weight of the washing or cleaning agent.

Also preferably contained in the washing and cleaning agents according to the present invention are bleaching agents, which by preference represent and/or supply the substrate for the bleach catalysts according to the present invention. A "bleaching agent" is to be understood in this context on the one hand as hydrogen peroxide itself and on the other hand as any compound that supplies hydrogen peroxide in an aqueous medium. Among the compounds yielding $H_2O_2$ in water and serving as bleaching agents, sodium percarbonate, sodium perborate tetrahydrate, and sodium perborate monohydrate are of particular importance. Other usable bleaching agents are, for example, peroxypyrophosphates, citrate perhydrates, and peracid salts or peracids that yield $H_2O_2$, such as persulfates or persulfuric acid. Also usable is the urea peroxohydrate percarbamide, which can be described by the formula $H_2N\text{—}CO\text{—}NH_2H_2O_2$. Especially when the agents are used for cleaning hard surfaces, for example in automatic dishwashing, they can if desired also contain bleaching agents from the group of the organic bleaching agents, although the use thereof is also possible, in principle, in agents for textile laundering. Typical organic bleaching agents are the diacyl peroxides such as, for example, dibenzoyl peroxide. Further typical organic bleaching agents are the peroxy acids, the alkylperoxy acids and arylperoxy acids being mentioned in particular as examples. Preferred representatives are (a) peroxybenzoic acid and its ring-substituted derivatives, such as alkylperoxybenzoic acids, but also peroxy-α-naphthoic acid and magnesium monoperphthalate; (b) the aliphatic or substituted aliphatic peroxy acids, such as peroxylauric acid, peroxystearic acid, ε-phthalimidoperoxycaproic acid (phthaloiminoperoxyhexanoic acid, PAP), o-carboxybenzamidoperoxycaproic acid, N-nonenylamidoperadipic acid, and N-nonenylamidopersuccinates; and (c) aliphatic and araliphatic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid, N,N-terephthaloyl-di(6-aminopercaproic) acid.

Substances that release chlorine or bromine can also be used as bleaching agents. Possibilities among the suitable materials releasing chlorine or bromine are, for example, heterocyclic N-bromamides and N-chloramides, for example trichloroisocyanuric acid, tribromoisocyanuric acid, dibromoisocyanuric acid, and/or dichloroisocyanuric acid (DICA), and/or salts thereof with cations such as potassium and sodium. Hydantoin compounds, such as 1,3-dichloro-5,5-dimethylhydantoin, are likewise suitable.

In a particular embodiment according to the present invention, the use of substances that supply hydrogen peroxide is omitted, and oxygen is used instead as a bleaching agent; the oxygen can in this context be atmospheric oxygen, or oxygen that is released from an oxygen-supplying agent.

Washing or cleaning agents, in particular automatic dishwashing agents, that contain up to 45 wt %, in particular 1 to 35 wt %, by preference 2.5 to 30 wt %, particularly preferably 3.5 to 20 wt %, and in particular 5 to 15 wt % bleaching agent, by preference sodium percarbonate, are preferred according to the present invention.

The active oxygen content of the washing or cleaning agent, in particular of the automatic dishwashing agent, is by preference between 0.4 and 10 wt %, particularly preferably between 0.5 and 8 wt %, and in particular between 0.6 and 5 wt %, based in each case on the total weight of the agent. Particularly preferred agents have an active oxygen content above 0.3 wt %, preferably above 0.7 wt %, particularly preferably above 0.8 wt %, and in particular above 1.0 wt %.

Alternatively to and simultaneously with the bleaching agents, enzymes that are capable of generating hydrogen peroxide in situ on the basis of other substrates can also be used to make hydrogen peroxide available. This relates to oxidoreductases, which can transfer electrons from (as a rule) an organic substrate, for example glucose, to oxygen as an electron acceptor, and thus enable the formation in situ of the desired hydrogen peroxide. The oxidoreductase can be used in this context together with the corresponding organic substrate. Because the stains to be treated may already contain the necessary substrate, however, the oxidoreductases can be used, if applicable, even without addition of the corresponding substrate.

The oxidoreductase that generates hydrogen peroxide is by preference an oxidoreductase that produces hydrogen peroxide by using oxygen as an electron acceptor. Suitable in this context, in particular, are oxidoreductases of EC classes E.C. 1.1.3 (CH—OH as electron donor), E.C. 1.2.3 (aldehyde or oxo group as electron donor), E.C. 1.4.3 (CH—NH$_2$ as donor), E.C. 1.7.3 (N-containing group as donor), and E.C. 1.8.3 (S-containing group as donor), enzymes of EC class E.C. 1.1.3 being preferred.

Preferred enzymes are selected, in particular, from the group made up of malate oxidase (EC 1.1.3.3), glucose oxidase (EC 1.1.3.4), hexose oxidase (EC 1.1.3.5), cholesterol oxidase (EC 1.1.3.6), galactose oxidase (EC 1.1.3.9), pyranose oxidase (EC 1.1.3.10), alcohol oxidase (EC 1.1.3.13), choline oxidase (EC 1.1.3.17, see esp. WO 04/58955), oxidases for long-chain alcohols (EC 1.1.3.20), glycerol-3-phosphate oxidase (EC 1.1.3.21), cellobiose oxidase (EC 1.1.3.25), nucleoside oxidase (EC 1.1.3.39), D-mannitol oxidase (EC 1.1.3.40), xylitol oxidase (EC 1.1.3.41), aldehyde oxidase (EC 1.2.3.1), pyruvate oxidase (EC 1.2.3.3), oxalate oxidase (EC 1.2.3.4), glyoxylate oxidase (EC 1.2.3.5), indole-3-acetaldehyde oxidase (EC 1.2.3.7), pyridoxal oxidase (EC 1.2.3.8), arylaldehyde oxidase (EC 1.2.3.9), retinal oxidase (EC 1.2.3.11), L-amino acid oxidase (EC 1.4.3.2), amine oxidase (EC 1.4.3.4, EC 1.4.3.6), L-glutamate oxidase (EC 1.4.3.11), L-lysine oxidase (EC 1.4.3.14), L-aspartate oxidase (EC 1.4.3.16), tryptophan-alpha,beta oxidase (EC 1.4.3.17), glycine oxidase EC 1.4.3.19), urea oxidase (EC 1.7.3.3), thiol oxidase (EC 1.8.3.2), glutathione oxidase (EC 1.8.3.3), sorbitol oxidase, and from enzymes such as those described in DE102005053529.

In a preferred embodiment, the hydrogen peroxide-producing oxidoreductase is one that uses a sugar as an electron donor. The hydrogen peroxide-producing and sugar-oxidizing oxidoreductase is by preference selected, according to the present invention, from glucose oxidase (EC 1.1.3.4), hexose oxidase (EC 1.1.3.5), galactose oxidase (EC 1.1.3.9), and pyranose oxidase (EC 1.1.3.10). Glucose oxidase (EC 1.1.3.4) is particularly preferred according to the present invention.

Advantageously, when a hydrogen peroxide-generating oxidoreductase is used, preferably organic, particularly preferably aromatic compounds interacting with the enzymes are additionally added in order to intensify the activity of the relevant oxidoreductases (enhancers) or, when the redox potentials between the oxidizing enzymes and the stains are very different, in order to ensure electron flow (mediators).

The hydrogen peroxide-producing oxidoreductase is utilized in the washing and cleaning agents according to the present invention, if it is used, by preference in a quantity such that the entire agent has an enzyme activity, based on the oxidoreductase, from 30 U/g to 20,000 U/g, in particular from 6 U/g to 15,000 U/g. The unit of 1 U (=unit) corresponds here to the activity of that quantity of enzyme that converts 1 μmol of its substrate at pH 7 and 25° C. in 1 minute.

The substrate to be used, if applicable, when a hydrogen peroxide-producing oxidoreductase of this kind is utilized is, as a rule, immediately apparent from the designation of the respective oxidoreductase.

Agents according to the present invention can also, if applicable, contain bleach activators as an additional bleaching adjuvant. Reference is made to Application WO 2008/135337 with regard to bleach activators preferably usable according to the present invention and the preferred utilization quantities thereof.

In addition to a bleach catalyst according to the present invention and the aforementioned bleaching agents and optionally contained further bleaching adjuvants, a washing or cleaning agent according to the present invention contains, if applicable, further ingredients such as further enzymes, enzyme stabilizers, surfactants, in particular nonionic, anionic, cationic, and/or amphoteric surfactants, detergency builders (builders, cobuilders), polymers, solvents, thickeners, sequestering agents, electrolytes, acidifying agents, optical brighteners, graying inhibitors, glass corrosion inhibitors, corrosion inhibitors, color transfer inhibitors, foam inhibitors, disintegration adjuvants, abrasives, dyes, fragrances, microbial active substances, UV absorbers, wrinkle-prevention agents, antistatic agents, so-called soil release active substances or soil repellents, propellants, and further usual ingredients as applicable.

With regard to further enzymes, enzyme stabilizers, surfactants, detergency builders, polymers, solvents, thickeners, sequestering agents, electrolytes, acidifying agents, optical brighteners, graying inhibitors, glass corrosion inhibitors, corrosion inhibitors, color transfer inhibitors, foam inhibitors, disintegration adjuvants, abrasives, dyes, fragrances, microbial active substances, UV absorbers, wrinkle-prevention agents, antistatic agents, soil release active substances, and propellants usable by preference according to the present invention, and to the preferred utilization quantities thereof, reference is made to Application WO 2008/135337.

Those bleach catalyst granules that contain, based on the total weight of the granule,
  a) 0.1 to 30 wt % of a bleach catalyst according to the present invention as well as, if applicable, further bleach catalyst,
  b) 10 to 99 wt % of a carrier material, and
  c) 0.1 to 5 wt % of a binding agent from the group of the organic polymers,
have proven to be particularly advantageous.

The further bleach catalyst according to a) that is to be used as applicable is by preference selected from the further bleach catalysts already recited previously.

Suitable as carrier material b) are, in principle, all substances or substance mixtures, in particular the detergency builders already listed previously, especially the carbonates including the hydrogencarbonates, the sulfates, the chlorides, the silicates, and the phosphates, that are usable in washing and cleaning agents and compatible with the other ingredients. Particularly suitable in this context as a carrier material are alkali metal carbonates, alkali metal hydrogencarbonates, alkali metal sesquicarbonates, alkali silicates, alkali metasilicates, alkali phosphates, and mixtures of said substances, wherein the alkali carbonates, in particular sodium carbonate, sodium hydrogencarbonate or sodium sesquicarbonate, and/or alkali phosphates, are used preferably for purposes of this invention. In a particularly preferred embodiment, pentasodium triphosphate, $Na_5P_3O_{10}$ (sodium tripolyphosphate) or the corresponding potassium salt pentapotassium triphosphate, $K_5P_3O_{10}$ (potassium tripolyphosphate) is used as a carrier material.

The weight proportion of carrier material b) in terms of the total weight of the bleach catalyst granules can be varied within the limits indicated above; in terms of processability and actual bleach performance after preparation with further ingredients having washing and cleaning activity, weight proportions above 20 wt %, by preference above 40 wt %, and in particular above 60 wt % have proven, in particular, to be advantageous. Bleach catalyst granules in which the weight proportion of carrier material b) in terms of the total weight of the granule is equal to 20 to 99 wt %, by preference between 40 and 95 wt %, and in particular between 60 and 90 wt %, are consequently preferred in the context of the present Application.

As a third ingredient, the bleach activator granules according to the present invention contain a binding agent c) from the group of the organic polymers. The polymers can be nonionic, anionic, cationic, or amphoteric in nature. Natural polymers and modified polymers of natural origin are usable, as are synthetic polymers.

The group of nonionic polymers used with particular preference as binding agent c) includes polyvinyl alcohols, acetalized polyvinyl alcohols, polyvinylpyrrolidones, and polyalkylene glycols, in particular polyethylene oxides. Preferred polyvinyl alcohols and acetalized polyvinyl alcohols have a molecular weight in the range from 10,000 to 100,000 gmol$^{-1}$, by preference from 11,000 to 90,000 gmol$^{-1}$, particularly preferably from 12,000 to 80,000 gmol$^{-1}$, and in particular from 13,000 to 70,000 gmol$^{-1}$. Preferred polyethylene oxides have molar weights in the range from approx. 200 to 5,000,000 g/mol, corresponding to degrees of polymerization n from approx. 5 to >100,000.

Members of the group of anionic polymers used with particular preference as binding agent c) are, in particular, homo- or copolymeric polycarboxylates, polyacrylic acids, and polymethacrylic acids, in particular those that have already been recited previously as organic builder substances usable for washing and cleaning agents, as well as sulfonic acid group-containing polymers, in particular those that have already been recited previously as usable softeners.

With regard to the group of cationic and amphoteric polymers used with particular preference as binding agent c), reference is made to the polymers already listed previously as polymers having washing and cleaning activity.

In bleach catalyst granules preferred according to the present invention, the weight proportion of binding agent c) in terms of the total weight of the granule is between 0.2 and 4.5 wt %, preferably between 0.5 and 4.0 wt %, and in particular between 1.0 and 4.0 wt %.

The bleach catalyst granules preferably possess an average particle size between 0.1 and 1.0 mm, particularly preferably between 0.2 and 0.8 mm, and in particular between 0.3 and 0.7 mm, wherein the weight proportion of particles having a particle size less than 0.1 mm is by preference at least 4 wt %, particularly preferably at least 6 wt %, and in particular at least 8 wt %, but at the same time by preference at most 80 wt %, particularly preferably at most 60 wt %, and in particular at most 40 wt %, and the weight proportion of particles having a particle size between 0.2 and 0.8 mm is by preference between 30 and 70 wt %, particularly preferably between 45 and 65 wt %, and in particular between 40 and 60 wt %.

In addition to the bleach catalyst, it is also possible for enzymes or other (in particular, sensitive) ingredients to be prepared in the manner described above.

A separate subject of the invention is represented by methods for cleaning textiles or hard surfaces in which a bleach catalyst according to the present invention is used at least in one of the method steps.

Included thereamong are both manual and automatic methods. Embodiments are represented by, for example, hand laundering, manual removal of spots from textiles or from hard surfaces, or utilization in connection with an automatic method, wherein automatic methods are preferred, in particular for cleaning textiles, because of their more precise controllability with regard, for example, to contact times and quantities used. The concentration ranges referred to above apply in correspondingly preferred fashion to these applications.

The cleaning of textile fabrics is accomplished by preference at temperatures from 20 to 95° C., in a preferred embodiment at temperatures from 20 to 60° C., in particular at temperatures from 20 to 40° C., and by preference at a pH from 5 to 12, in particular from 8 to 11.

Methods for cleaning textiles are generally notable for the fact that, in multiple method steps, different substances having cleaning activity are applied onto the material to be cleaned and are washed off after the contact time, or that the material to be cleaned is treated in another manner with a washing agent or with a solution of said agent. The same applies to methods for cleaning all materials other than textiles, which are grouped under the term "hard surfaces." All conceivable washing or cleaning methods can be enriched, in at least one of the method steps, with a bleach catalyst according to the present invention, and then represent embodiments of the present invention.

In a preferred embodiment of this use, the bleach catalysts according to the present invention are made available in the context of one of the formulations set forth above for agents according to the present invention, by preference washing or cleaning agents, respectively.

A further subject of the present invention is also a product containing a composition according to the present invention or a washing or cleaning agent according to the present invention, in particular a cleaner according to the present invention for hard surfaces, and a spray dispenser. The product can in this context be both a single-chamber and a multi-chamber vessel, in particular a two-chamber vessel. In this context, the spray dispenser is preferably a manually activated spray dispenser, selected in particular from the group encompassing aerosol spray dispensers (pressurized-gas containers, also referred to inter alia as a spray can), spray dispensers that themselves build up pressure, pump spray dispensers, and trigger spray dispensers, in particular pump spray dispensers and trigger spray dispensers having a container made of transparent polyethylene or polyethylene terephthalate. Spray dispensers are described more exhaustively in WO 96/04940 (Procter & Gamble) and in the U.S. patents cited therein regarding spray dispensers, to which patents in their entirety reference is made in this regard, and the content of which is hereby incorporated into this Application. Trigger spray dispensers and pump atomizers possess the advantage, as compared with pressurized-gas containers, that no propellant needs to be used. By means of suitable particle-capable attachments, nozzles, etc. (so-called "nozzle valves") on the spray dispenser, in this embodiment an enzyme that may be contained can optionally also be added to the agent in a form immobilized on particles, and thus metered as a cleaning foam.

Automatic dishwashing agents particularly preferred according to the present invention encompass

- 5 to 70 wt %, by preference 10 to 60 wt %, and in particular 20 to 50 wt % detergency builder(s) with the exception of polymers having washing and cleaning activity;
- 2 to 28 wt %, by preference 4 to 20 wt %, and in particular 6 to 15 wt % polymers having washing and cleaning activity;
- 0.5 to 10 wt %, by preference 1 to 8 wt %, and in particular 2 to 6 wt % surfactant(s), by preference nonionic and/or amphoteric surfactant(s);
- 0.5 to 8 wt %, by preference 1 to 7 wt %, and in particular 2 to 6 wt % enzyme(s);
- 2 to 20 wt %, by preference 4 to 15 wt %, and in particular 6 to 12 wt % bleaching agent;
- 0.01 to 5 wt %, by preference 0.02 to 4 wt %, and in particular 0.05 to 3 wt % bleach catalysts according to the present invention; and, if applicable,
- 0.01 to 5 wt %, by preference 0.02 to 4 wt %, and in particular 0.05 to 3 wt % further bleach catalysts.

Very particularly preferred automatic dishwashing agents encompass

- 5 to 70 wt %, by preference 10 to 60 wt %, and in particular 20 to 50 wt % phosphates;
- 2 to 28 wt %, by preference 4 to 20 wt %, and in particular 6 to 15 wt % polymers having washing and cleaning activity;
- 0.5 to 10 wt %, by preference 1 to 8 wt %, and in particular 2 to 6 wt % nonionic surfactant(s);

0.5 to 8 wt %, by preference 1 to 7 wt %, and in particular 2 to 6 wt % enzyme(s) selected from amylases, proteases, and amadoriases;

2 to 20 wt %, by preference 4 to 15 wt %, and in particular 6 to 12 wt % percarbonate;

0.01 to 5 wt %, by preference 0.02 to 4 wt %, and in particular 0.05 to 3 wt % bleach catalysts according to the present invention; and, if applicable, 0.01 to 5 wt %, by preference 0.02 to 4 wt %, and in particular 0.05 to 3 wt % further bleach catalysts.

Automatic dishwashing agents according to the present invention can be prepared in various ways. The agents according to the present invention can be present in solid or liquid presentation forms, and as a combination of solid and liquid presentation forms.

Powders, granules, extrudates, or compactates, in particular tablets, are suitable in particular as solid presentation forms. The liquid presentation forms, based on water and/or organic solvents, can be present in thickened fashion in the form of gels.

Agents according to the present invention can be prepared in the form of single-phase or multi-phase products. Automatic dishwashing agents having one, two, three, or four phases are particularly preferred. Automatic dishwashing agents, present in the form of a prefabricated dispensing unit having two or more phases, are particularly preferred.

The individual phases of multi-phase agents can have the same or different aggregate states. Automatic dishwashing agents that comprise at least two different solid phases and/or at least two liquid phases and/or at least one solid and at least one solid phase are preferred in particular.

Automatic dishwashing agents according to the present invention are preferably pre-packaged into dispensing units. These dispensing units preferably encompass the quantity of substances having washing or cleaning activity that is necessary for one cleaning cycle. Preferred dispensing units have a weight between 12 and 30 g, preferably between 14 and 26 g, and in particular between 16 and 22 g.

With particular preference, the volume of the aforesaid dispensing units, and their three-dimensional shape, are selected so that dispensability of the pre-packaged units via the dispensing chamber of an automatic dishwasher is guaranteed. The volume of the dispensing unit is therefore preferably between 10 and 35 ml, by preference between 12 and 30 ml, and in particular between 15 and 25 ml.

The automatic dishwashing agents according to the present invention, in particular the prefabricated dispensing agents, particularly preferably possess a water-soluble casing.

The Examples that follow describe the invention further without limiting it thereto.

EXEMPLIFYING EMBODIMENTS

Example 1

Preparation of the bisq Complexes Used

[Mn$_3$(bisq)$_2$(L)$_2$(OAc)$_2$]

3 C$_{19}$H$_{15}$N$_3$O$_2$+2 Mn(OAc)$_2$*4H$_2$O→[Mn$_3$(N-Me-bisq)$_2$(L)$_2$(OAc)$_2$]

3 C$_{22}$H$_{21}$N$_3$O$_2$+2 Mn(OAC)$_2$*4H$_2$O→[Mn$_3$(N-nBu-bisq)$_2$(L)$_2$(OAc)$_2$]

Preparation of the Complexes is Achieved by Reacting the Corresponding Bisq ligand with 1.5 equivalents of manganese(II) acetate tetrahydrate in methanol.

For this, 3 mmol of the respective ligand (Fluka) is weighed, combined with 30 ml methanol or ethanol, and heated in reflux. This is followed by the addition of 1 mmol Mn(OAc)$_2$ as a solid or a methanol solution; a suspension of an orange solid in yellowish solution forms almost immediately. After cooling to room temperature, the complex can be separated out quantitatively as an orange, finely crystalline solid.

[Mn$_3$(N-nBu-bisq)$_2$(L)$_2$(OAc)$_2$]:

IR (KBr): 3039, 2964, 2799, 1616, 1589, 1559, 1497, 1469, 1441, 1386, 1373, 1332, 1288, 1214, 1132, 1288, 1214, 1132, 1100, 1046, 858, 824, 794, 744, 661, 592, 540, 514, 430 cm$^{-1}$.

Comp. crystal structure: JDK51

[Mn(bisq)(H$_2$O)]$_2$ (C$_{19}$H$_3$N$_3$O$_2$)(NH$_4^+$)$_2$+Mn(OAc)$_2$*4H$_2$O→[Mn(N-Me-bisq)(L)]

(C$_{22}$H$_{19}$N$_3$O$_2$)(NH$_4^+$)$_2$+Mn(OAc)$_2$*4H$_2$O→[Mn(N-nBu-bisq)(L)]

Preparation of the Complexes is Achieved by Reacting the Corresponding Bisq ligand with 1 equivalent of manganese (II) acetate tetrahydrate in an ammonia environment.

1 mmol of the respective ligand (Fluka) is weighed, combined with 30 ml methanol and 10 drops of concentrated ammonia, and heated in reflux. This is followed by the addition of 1 mmol Mn(OAc)$_2$ as an aqueous solution. After cooling to room temperature, the complex can be separated out quantitatively as an orange, crystalline solid.

[Mn(NnBu-bisq)(H$_2$O)]$_2$:

IR (KBr): 2928, 2858, 1640, 1613, 1586, 1555, 1495, 1443, 1383, 1333, 1301, 1199, 1154, 1130, 1097, 1025, 997, 965, 860, 816, 787, 749, 733, 706, 664, 645, 590, 560, 512 cm$^{-1}$.

Example 2

Test of the Mn—N-n-Bu-bisq Complex for Damage and Primary Washing Performance in the Miniaturized Washing Test Mn-bisq complexes where R=hydrogen (bisq), n-butyl (N-n-Bu-bisq), or R=methyl (N-n-Me-bisq)

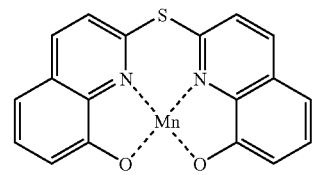

Mn—S-bisq Complex

The primary washing power and wet breaking load loss were tested in a miniaturized washing test, working with a complete liquid laundry detergent formulation. The pH values in the liquid formulation were adjusted with NaOH so that for a dispensing rate of 4.4 gal and after addition of the other additives, the respective pH existed in the washing formulation. 4.4 g/l liquid laundry detergent, 0.35 g/l H$_2$O$_2$, and 3.6 mg/l Mn—N-nBu-bisq were added to water at 16° dH. The cavities of the MLA were each filled with 10 ml of the washing liquor.

For primary washing performance, a cotton substrate having the respective stain was clamped in the sample container and the container was rotated in the microwave for 1 h at the indicated temperature so that the liquid in the cavities was constantly in contact with the cotton. The treated fabric substrate was rinsed under running lukewarm water and then dried and color-measured.

For wet breaking load loss, a cotton strip of defined width (number of threads) was placed into each cavity of the sample container, and the container was rotated in the microwave for 1 h at 60° C. This treatment was repeated 20 times. The strips were dried and dipped into a wetting solution before being torn with a tensile testing machine at a constant test speed. The tearing force of the treated cotton was compared with the tearing force of the untreated cotton, and the wet breaking load loss was calculated as a percentage.

Five determinations were made for primary washing power and for wet breaking load loss.

TABLE 1

Experimental results for Mn—N-nBu-bisq

| pH | Primary washing power (Y value) BC1, T = 30° C. | Primary washing power (Y value) BC3, T = 30° C. | Primary washing power (Y value) BC1, T = 60° C. | Wet breaking load loss [%] |
|---|---|---|---|---|
| 7  | 48.1 | 47   | 49.2 | 7  |
| 8  | 47.9 | 46.9 | 50.8 | 5  |
| 9  | 48.9 | 46.8 | 52   | 5  |
| 10 | 49.6 | 48.1 | 54.9 | 5  |
| 11 | 51.4 | 50.2 | 58.6 | 10 |

For comparison, the results for the bleach catalyst Mn-TACN are presented below.

TABLE 2

Experimental results for Mn-TACN

| pH | Primary washing power (Y value) BC1, T = 30° C. | Primary washing power (Y value) BC3, T = 30° C. | Primary washing power (Y value) BC1, T = 60° C. | Wet breaking load loss [%] |
|---|---|---|---|---|
| 7  | 50.4 | 48.4 | n.d. | 20 |
| 8  | 52.0 | 51.3 | n.d. | 31 |
| 9  | 53.8 | 54.4 | n.d. | 33 |
| 10 | 57.0 | 56.2 | n.d. | 57 |
| 11 | 60.3 | 58.5 | n.d. | 83 |

It is evident that the primary washing power of the Mn—N-nBu-bisq complex at 30° C. at the various pH values tested is weaker overall than that of Mn-TACN, but its value is still acceptable. The great advantage as compared with Mn-TACN is that the wet breaking load loss with the use of Mn—N-nBu-bisq is much less than when Mn-TACN is used, so that the overall quotient between washing power and damage is much better for Mn—N-nBu-bisq than for Mn-TACN.

Example 3

Washing Tests in a Model Washing Facility

The washing test is carried out in a temperature-controllable multi-agitator apparatus.

The test vessels used are 1-liter beakers in which an apparatus is present for mechanically stirring the washing bath. The stirring mechanism is designed so that on the one hand all the beakers are stirred at the same speed, and on the other hand the stirring direction periodically changes. The washing chambers are loaded with approx. 16 g of ballast laundry and approx. 6 g of stained fabric (the fabric pieces are cut into a square shape approx. 6 cm on a side and are made of cotton). All the test fabrics are manufactured by CFT B.V. (Netherlands).

The stained fabrics involve the following bleach-relevant test substrates:

| CS-103 | red wine |
| CS-3   | red wine, aged |
| BC-1   | tea |
| BC-3   | tea |
| CS-15  | bilberry juice |

From these five test fabrics, a set of eight stained fabric pieces was assembled for the tests. This means that three stains are represented twice in the test.

In order to ascertain bleaching performance, the tristimulus value Y (brightness value) of the bleached fabric was determined, and was compared with the reference samples. The tristimulus value Y is calculated from the measured L value using the following mathematical relationship:

$$L = 116(Y/Y_n)^{1/3} - 16.$$

Measurement of the L values is carried out using a Minolta CM-508d spectrophotometer. Two basic scenarios are utilized for washing tests in order to determine bleaching activity: on the one hand, washing tests using a complete laundry detergent formulation without TAED (washing test with complete laundry detergent without TAED), and on the other hand a simplified washing test that contains only hydrogen peroxide and surfactants ($H_2O_2$ test). The following test parameters are used for the washing testing with a complete laundry detergent without TAED:

Volume of laundry detergent solution: 750 ml
Quantity of laundry detergent with TAED: (100 g CLD per 16 l of bath, hence 4.69 g per 750 ml)
Quantity of laundry detergent without TAED: 4.55 g per 750 ml
Metal catalyst: 0.0086 mmol per transition metal atom
Temperature: 30° C.
Washing time: 60 min
Rinse volume: 500 ml
Rinsing time: 15
Water quality: deionized water artificially hardened with
  $CaCl_2 \times 2H_2O$ (8.73 g per 25 l) and
  $MgCl_2 \times 6H_2O$ (2.42 g per 25 l)=16° dH)
  pH 10.5 (carbonate buffer solution).

The washing results for the various transition metal complexes in a complete laundry detergent without TAED are shown in the table below. The value for a complete laundry detergent without TAED and without transition metal complexes ("no catalyst"), and the value for a complete laundry detergent with TAED, are shown as comparison values.

TABLE 3

Washing tests using complete laundry detergent without TAED

| Mn—N-nBu-bisq | 76 |
| Mn—N-Me-bisq  | 73 |
| no catalyst   | 71.7 |
| TAED          | 75.8 |

The following test parameters are used in the simplified washing test ($H_2O_2$ test):

Volume of laundry detergent solution: 750 ml
Quantity of $H_2O_2$: 10 mmol per liter
Surfactants: LAS=0.58 g; LT07=0.12 g
Metal catalyst: 0.0086 mmol per transition metal atom
Temperature: 30° C.
Washing time: 60 min Water quality: deionized water
pH: 10.5 (carbonate buffer solution)

The washing results for the various transition metal complexes according to the simplified washing test ($H_2O_2$ test) are shown in the table below:

TABLE 4

| Simplified washing test ($H_2O_2$ test) | |
|---|---|
| Mn—N—nBu-bisq | n.d. |
| Mn—N—Me-bisq | 75 |
| Mn—N—H-bisq | 75 |
| Mn—S-bisq | 75 |

The invention claimed is:

1. An agent for washing or cleaning a textile fabric, the agent comprising at least one component selected from the group consisting of ligands of the general formula (I), ligand-metal complexes of ligands of the general formula (I), and combinations thereof:

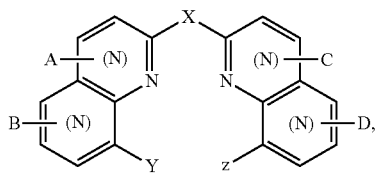
(I)

wherein X represents a moiety selected from the group consisting of $NR^1$, $NR^1R^{2(+)}$, $PR^1$, $PR^1R^{2(+)}$, $P(O)R^1$, O, S, $BR^1$, $BR^1R^{2(-)}$, $CR^3R^4$, or $SiR^3R^4$; wherein Y and Z each independently represents a substituent selected from the group consisting of OH, SH, $NH_2$, $NHR^5$, and $NR^5R^6$; wherein A, B, C, D, $R^1$, $R^2$, $R^3$, and $R^4$ each independently represents a substituent selected from the group consisting of hydrogen, alkyl, trifluoromethyl, cycloalkyl, cycloalkylalkyl, alkenyl, alkinyl, heteroalkyl, heterocycloalkyl, alkoxy, alkylsulfanyl, alkylsulfinyl, alkylsulfonyl, alkanoyl, alkanoyloxy, alkoxycarbonyl, alkylaminocarbonyl, alkylsulfanylcarbonyl, hydroxy, amino, aryl, arylalkyl, aryloxy, arylsulfanyl, arylsulfinyl, arylsulfonyl, arylcarbonyl, arylcarbonyloxy, aryloxycarbonyl, arylaminocarbonyl, arylsulfanylcarbonyl, heteroaryl, heteroarylalkyl, heteroaryloxy, heteroarylamino, heteroarylsulfanyl, heteroarylsulfonyl, heteroarylsulfoxidyl, heteroarylcarbonyl, heteroarylcarbonyloxy, heteroaryloxycarbonyl, heteroarylaminocarbonyl, heteroarylsulfanylcarbonyl, alkoxysulfonyl, alkoxycarbinol, ammonium, hydroxycarbonyl, alkoxycarbonyl, aryloxycarbonyl, amidocarbonyl, halogen, nitro, sulfato, sulfo, amidosulfo, phosphato, phosphono, amidophosphono, formyl, thioformyl, —($CH_2$—$CH_2$—O—)$_n$H and —($CH_2$—$CH_2$—$CH_2$—O)$_n$H where n=1 to 20; wherein $R^5$ and $R^6$ each independently represents hydrogen or alkyl; and wherein all residues of a so resulting molecule, mutually independently in each case, can optionally also be mono- or polysubstituted; and further comprising a surfactant.

2. The agent according to claim 1, wherein the at least one component is selected from the group consisting of ligands of the general formula (II), ligand-metal complexes of ligands of the general formula (II), and combinations thereof:

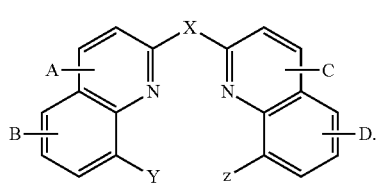
(II)

3. The agent according to claim 1, wherein the at least one component is selected from the group consisting of ligands of the general formula (III), ligand-metal complexes of ligands of the general formula (III), and combinations thereof:

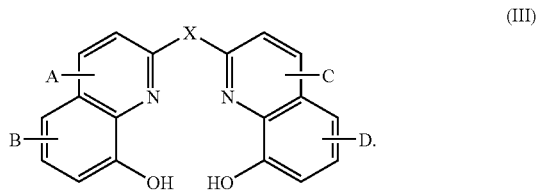
(III)

4. The agent according to claim 1, wherein $R^1$ and $R^2$ each independently represent hydrogen, alkyl, cycloalkyl, cycloalkylalkyl, alkenyl, alkinyl, heteroalkyl, heterocloalkyl, alkanoyl, alkoxycarbonyl, alkylaminocarbonyl, alkylsulfanylcarbonyl, aryl, arylalkyl, arylcarbonyl, aryloxycarbonyl, arylaminocarbonyl, arylsulfanylcarbonyl, heteroaryl, heteroarylalkyl, heteroarylcarbonyl, heteroaryloxycarbonyl, heteroarylaminocarbonyl, heteroarylsulfanylcarbonyl, trifluoromethyl, formyl, —($CH_2$—$CH_2$—O—)$_n$H or —($CH_2$—$CH_2$—$CH_2$—O)$_n$H where n=1 to 20, in which all residues of the so resulting molecule, mutually independently in each case, can optionally also be mono- or polysubstituted.

5. The agent according to claim 1, wherein X represents a moiety selected from the group consisting of $NR^1$, $NR^1R^{2(+)}$, $PR^1$, or $PR^1R^{2(+)}$.

6. The agent according to claim 1, wherein X represents a moiety selected from the group consisting of $NR^1$, $NR^1R^{2(+)}$, $PR^1$ or $PR^1R^{2(+)}$, wherein Y and Z each represent OH, wherein $R^1$ represent a moiety selected from the group consisting of hydrogen, $C_{1-6}$ alkyl, —($CH_2$—$CH_2$—O—)$_n$H or —($CH_2$—$CH_2$—$CH_2$—O)$_n$H where n=1 to 20, and wherein A, B, C, and D each independently represent hydrogen, alkyl, ammonium, hydroxycarbonyl, alkoxycarbonyl, aryloxycarbonyl, amidocarbonyl, halogen, nitro, sulfato, sulfo, amidosulfo, phosphato, phosphono, amidophosphono, hydroxy, alkoxy, or amino, in which all residues of the so resulting molecule, mutually independently in each case, can optionally also be mono- or polysubstituted.

7. The agent according to claim 1, wherein at least one of the residues A, B, C, D, and X comprises a group selected from ammonium, hydroxycarbonyl, alkoxycarbonyl, aryloxycarbonyl, amidocarbonyl, halogen, nitro, sulfato, sulfo, amidosulfo, phosphato, phosphono, amidophosphono, hydroxy, alkoxy, amino, and polyoxyethylene.

8. The agent according to claim 1, wherein the at least one component comprises a metal-ligand complex of ligands of the general formula (I) comprising a metal selected from the group consisting of Ag, Al, Ce, Co, Cu, Fe, Mo, Mn, Ni, Pb, Re, Ti, V, and Zn in any oxidation states.

9. A method comprising: (a) providing a textile fabric; and (b) contacting the textile fabric with an agent according to claim 1.

10. A method comprising: (a) providing a textile fabric; and (b) contacting the textile fabric with an agent according to claim 2.

11. A method comprising: (a) providing a textile fabric; and (b) contacting the textile fabric with an agent according to claim 3.

* * * * *